US010159431B2

(12) United States Patent  (10) Patent No.: US 10,159,431 B2
Parker et al.  (45) Date of Patent: Dec. 25, 2018

(54) DIGITAL PROFESSIONAL TRAINING INSTRUCTOR (THE DPT INSTRUCTOR)

(75) Inventors: Kermit Patrick Parker, Angola, LA (US); Gladys Parker, Baton Rouge, LA (US); Samuel Parker, Baton Rouge, LA (US)

(73) Assignee: Kermit Patrick Parker, St. Gabriel, LA (US)

( * ) Notice: Subject to any disclaimer, the term of this patent is extended or adjusted under 35 U.S.C. 154(b) by 569 days.

(21) Appl. No.: 12/930,359

(22) Filed: Jan. 5, 2011

(65) Prior Publication Data

US 2014/0213415 A1   Jul. 31, 2014

Related U.S. Application Data

(60) Provisional application No. 61/335,498, filed on Jan. 8, 2010.

(51) Int. Cl.
  *G09B 19/00* (2006.01)
  *A61B 5/11* (2006.01)
  (Continued)

(52) U.S. Cl.
  CPC .......... *A61B 5/1124* (2013.01); *A61B 5/1116* (2013.01); *A61B 5/1121* (2013.01);
  (Continued)

(58) Field of Classification Search
  CPC . G09B 19/0038; A61B 5/1121; A61B 5/1123; A63B 2220/16; A63B 2220/24;
  (Continued)

(56) References Cited

U.S. PATENT DOCUMENTS 5,826,578 A * 10/1998 Curchod .............. A61B 5/1121
                                                          434/252
5,976,063 A * 11/1999 Joutras ................. A43B 1/0054
                                                          482/114

(Continued)

*Primary Examiner* — Robert J Utama

(57) ABSTRACT

The DPT INSTRUCTOR provides unprecedented exercise instruction guidance by applying unparalleled precision and pinpoint accuracy that comes from combining professional exercise instructor expertise, physics and computer electronics. Considering the marketability of renowned professional/celebrity instructors who have their own unique style, technique, format and dedicated customers. The DPT INSTRUCTOR provides exclusive programming and formulation to guide and exact the expert training regiment of any fitness instructors individual form, execution, posture, expertise and technique. Regardless to the desired classification of an individual's type of training, age class, choice of workout machine/device, free weights, calisthenics, aerobics or physical constraints there are expert training instructors for all particular needs available for the DPT INSTRUCTOR programming systems by way of providing their very own unique and personalized execution/posture technique, "inso guaranteeing a convenience, guidance and interactive accessibility that was formerly unknown, unavailable and unattainable to the mainstream/professional exercise instruction guidance device marketing field".

18 Claims, 20 Drawing Sheets

(51) Int. Cl.
*G06F 19/00* (2018.01)
*A63B 21/072* (2006.01)
*A63B 23/02* (2006.01)

(52) U.S. Cl.
CPC ........ *A61B 5/1122* (2013.01); *G06F 19/3481* (2013.01); *G09B 19/0038* (2013.01); *A63B 21/072* (2013.01); *A63B 21/0726* (2013.01); *A63B 23/0222* (2013.01); *A63B 2220/16* (2013.01); *A63B 2220/24* (2013.01)

(58) Field of Classification Search
CPC ............ A63B 21/0726; A63B 21/0222; A63B 23/0222
USPC .................................................. 434/247, 252
See application file for complete search history.

(56) References Cited

U.S. PATENT DOCUMENTS

| | | | | |
|---|---|---|---|---|
| 6,064,912 | A * | 5/2000 | Kenney | A61F 5/0111 602/16 |
| 6,456,885 | B1 * | 9/2002 | Shiba | A61N 1/0452 607/48 |
| 6,941,239 | B2 * | 9/2005 | Unuma et al. | 702/141 |
| 7,602,301 | B1 * | 10/2009 | Stirling et al. | 340/573.1 |
| 7,825,815 | B2 * | 11/2010 | Shears | A61B 5/1127 340/573.1 |
| 7,981,057 | B2 * | 7/2011 | Stewart | A41D 13/02 600/587 |
| 8,043,173 | B2 * | 10/2011 | Menalagha | A63B 71/0622 473/450 |
| 8,140,339 | B2 * | 3/2012 | Hernandez-Rebollar | G06K 9/00355 382/182 |
| 8,452,458 | B2 * | 5/2013 | Even-Zohar | 700/279 |
| 8,504,201 | B2 * | 8/2013 | Moll et al. | 700/245 |
| 8,616,989 | B2 * | 12/2013 | Bentley | A61B 5/1122 473/207 |
| 2003/0181832 | A1 * | 9/2003 | Carnahan | A61B 5/4528 600/595 |
| 2004/0219498 | A1 * | 11/2004 | Davidson | A63B 69/00 434/247 |
| 2005/0113652 | A1 * | 5/2005 | Stark | A61F 5/0125 600/300 |
| 2005/0209049 | A1 * | 9/2005 | Shields | A61H 1/001 482/8 |
| 2006/0022833 | A1 * | 2/2006 | Ferguson | A63F 13/211 340/573.1 |
| 2006/0217233 | A1 * | 9/2006 | Lee | A61B 5/1071 482/9 |
| 2006/0235643 | A1 * | 10/2006 | Tokuyama | A63B 24/0003 702/150 |
| 2007/0155588 | A1 * | 7/2007 | Stark | A61F 5/0102 482/8 |
| 2008/0234781 | A1 * | 9/2008 | Einav | A61N 1/36014 607/48 |
| 2009/0024062 | A1 * | 1/2009 | Einarsson | A41D 13/1281 600/595 |
| 2009/0143704 | A1 * | 6/2009 | Bonneau | A61B 5/1038 600/595 |
| 2010/0015585 | A1 * | 1/2010 | Baker | A63B 24/0003 434/247 |
| 2010/0137749 | A1 * | 6/2010 | Jeong | A61B 5/1126 600/595 |
| 2012/0000300 | A1 * | 1/2012 | Sunagawa et al. | 73/865.4 |
| 2012/0046901 | A1 * | 2/2012 | Green | A61B 5/1126 702/141 |
| 2013/0115583 | A1 * | 5/2013 | Gordon | G06F 19/3418 434/247 |
| 2014/0107531 | A1 * | 4/2014 | Baldwin | A61B 5/165 600/595 |
| 2014/0135960 | A1 * | 5/2014 | Choi | A61B 5/0205 700/91 |
| 2014/0199672 | A1 * | 7/2014 | Davidson | A63B 69/00 434/247 |
| 2014/0228985 | A1 * | 8/2014 | Elliott | A63B 71/06 700/91 |
| 2015/0202492 | A1 * | 7/2015 | Domansky | A63F 13/00 434/257 |

\* cited by examiner

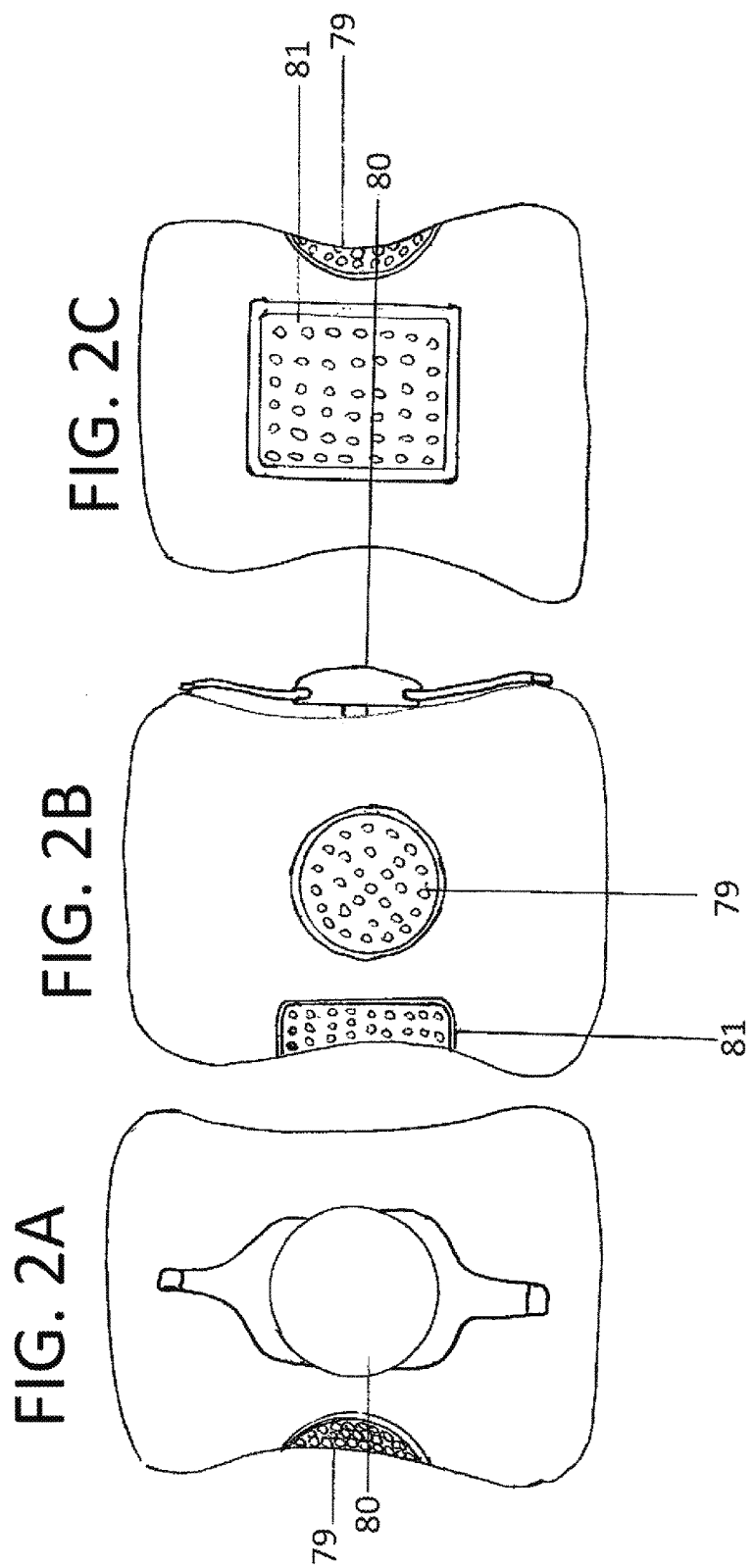

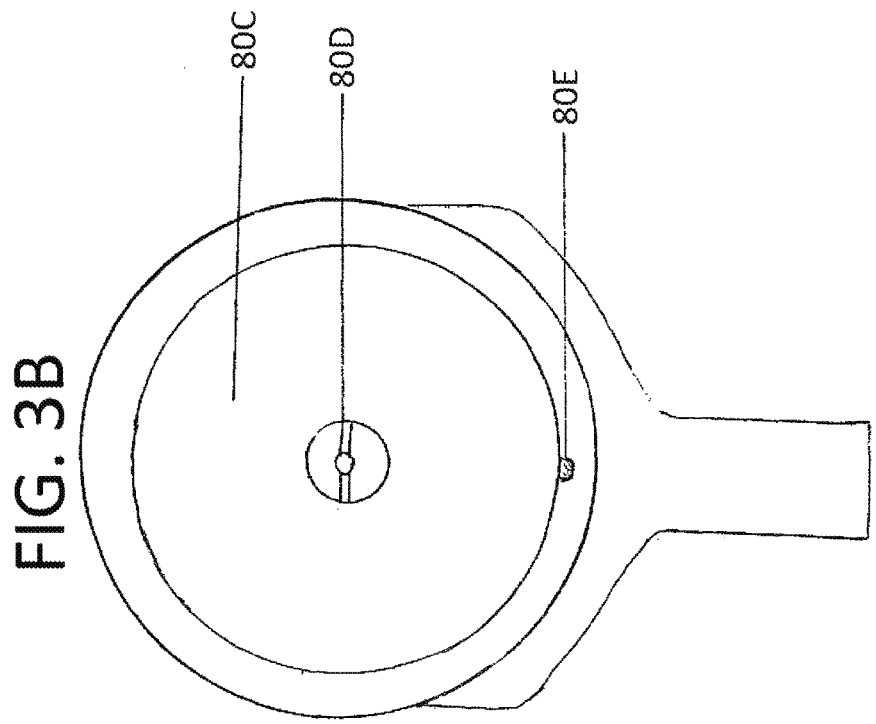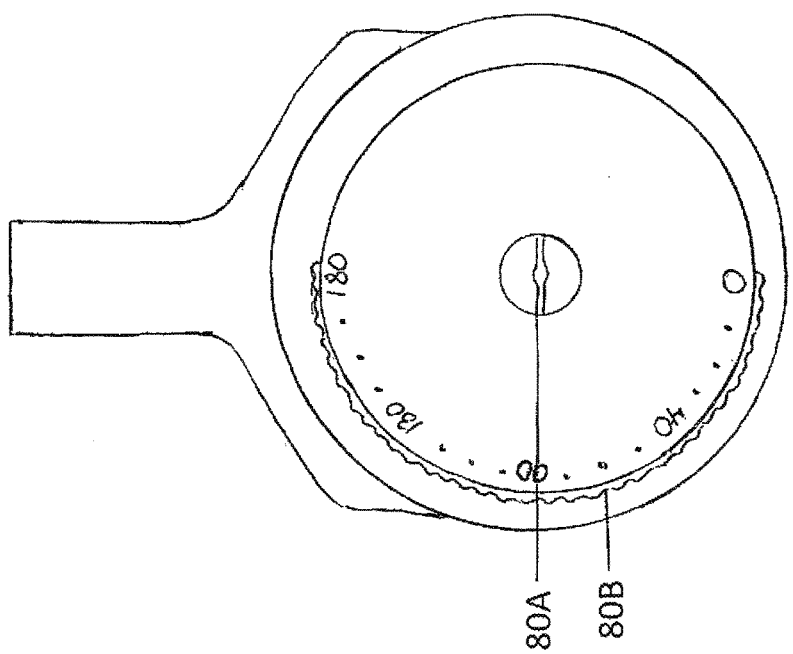

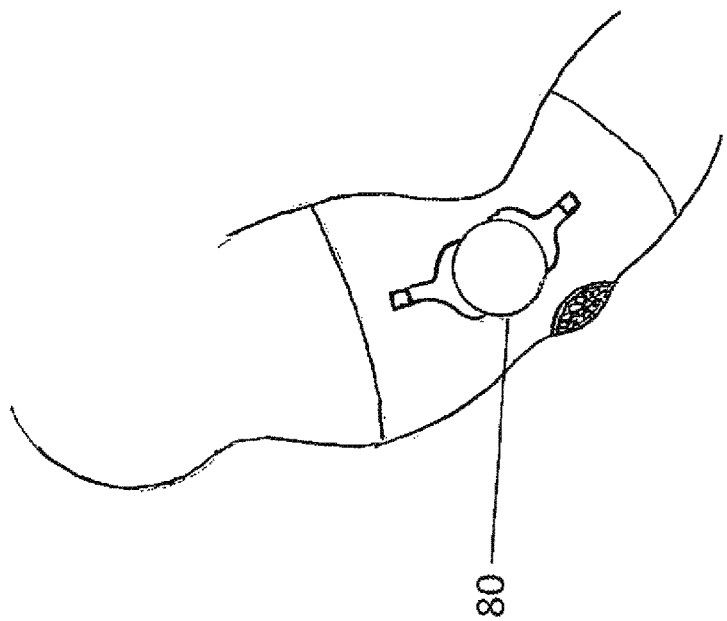
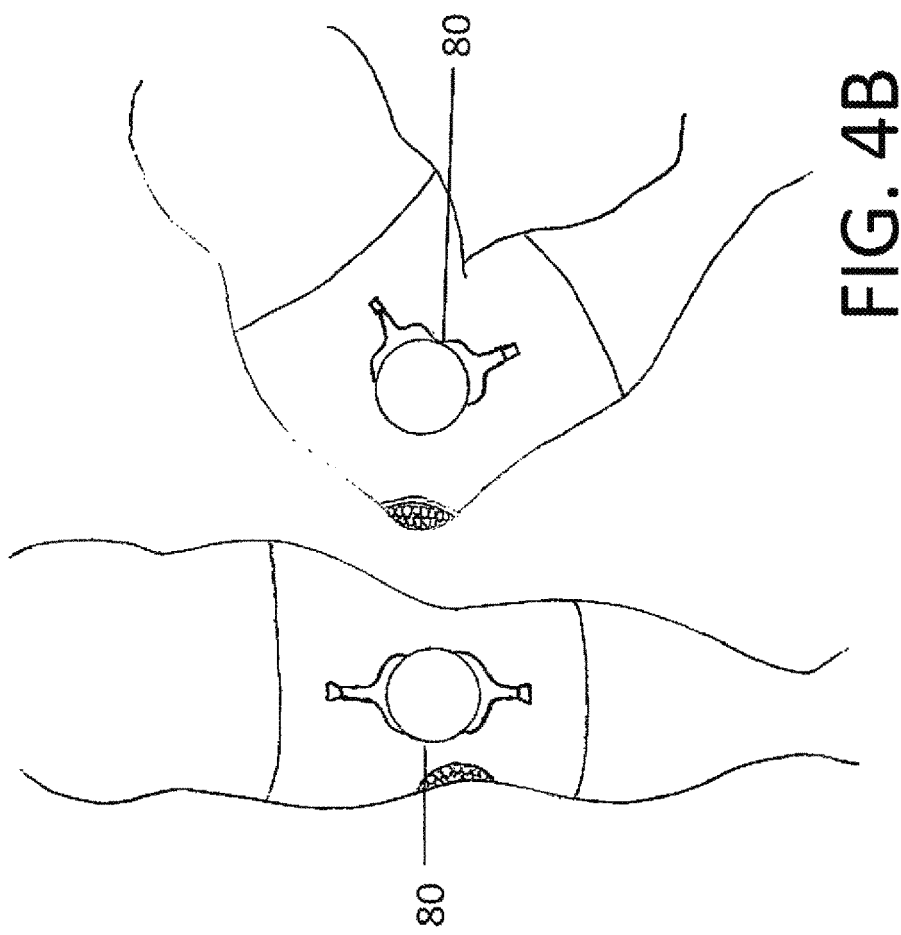
FIG. 4A  FIG. 4B  FIG. 4C

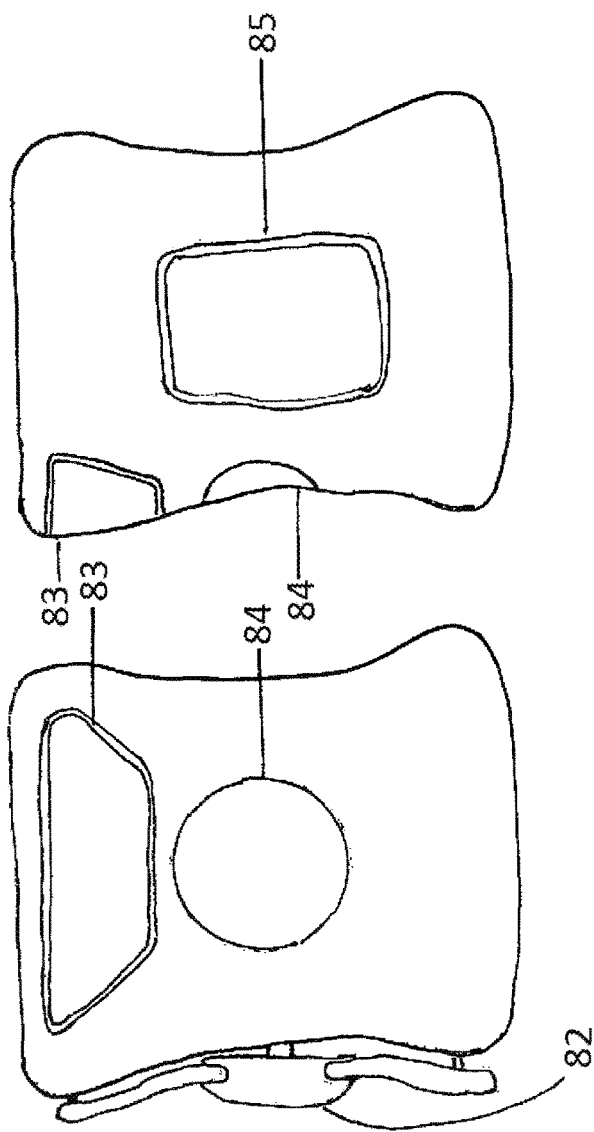

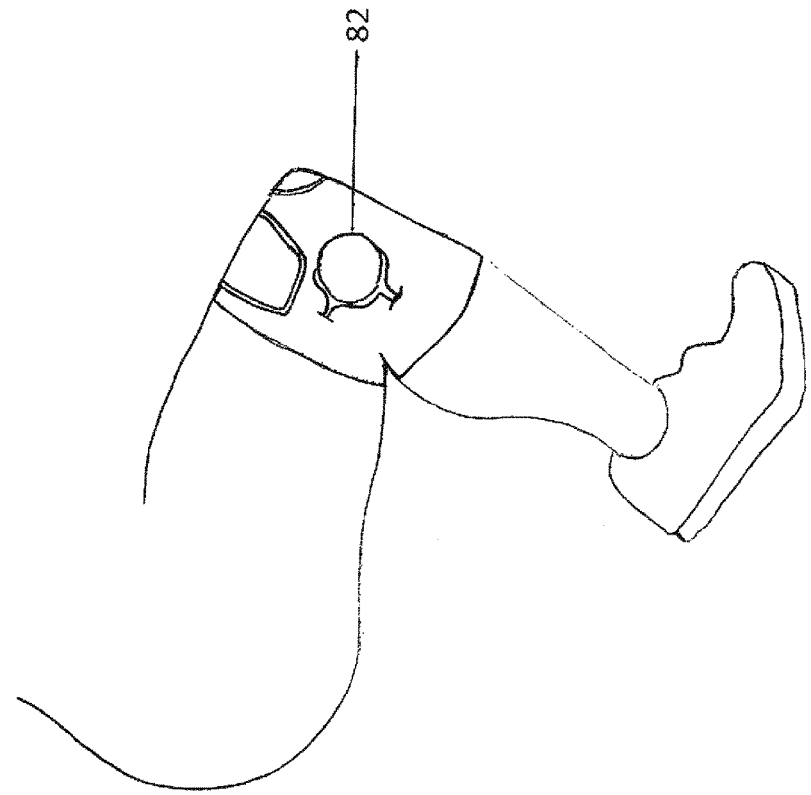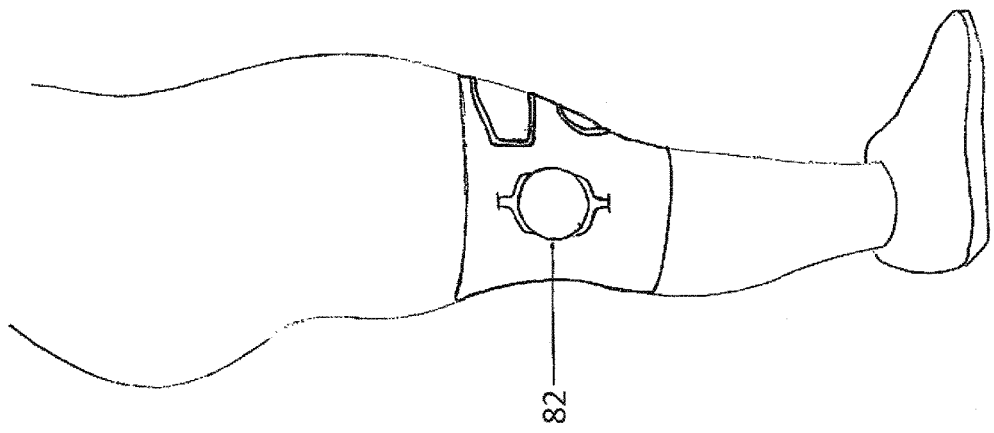

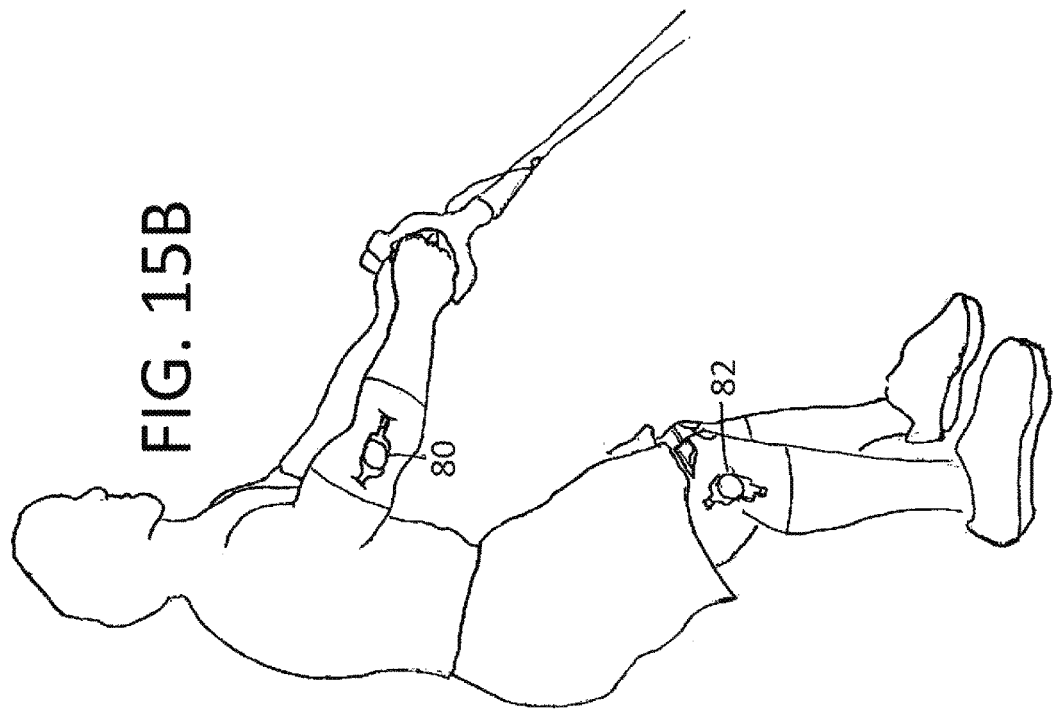
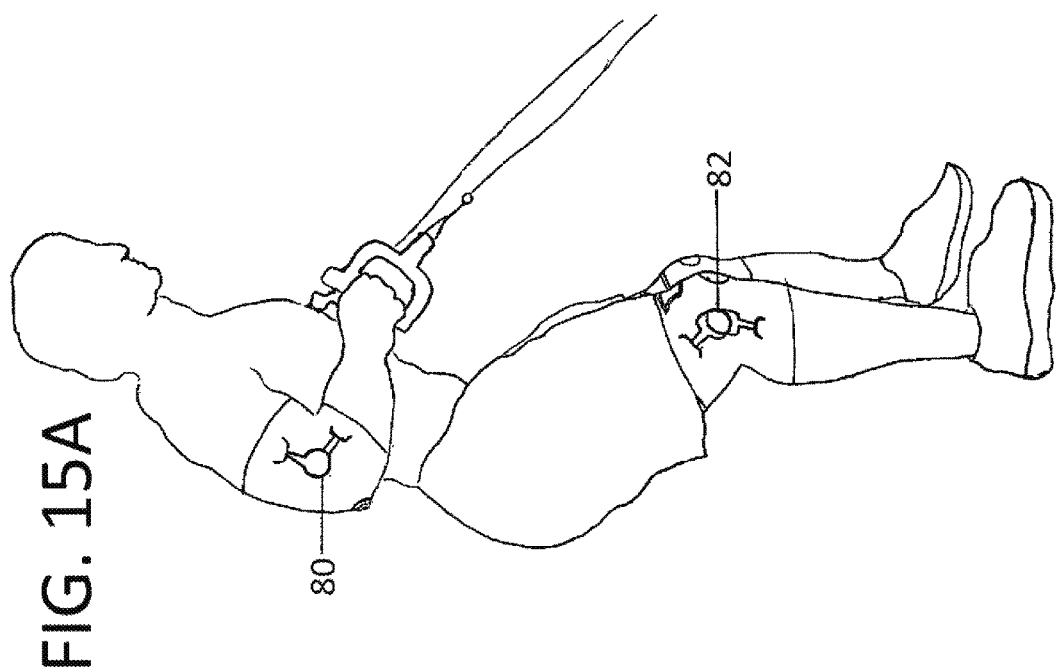

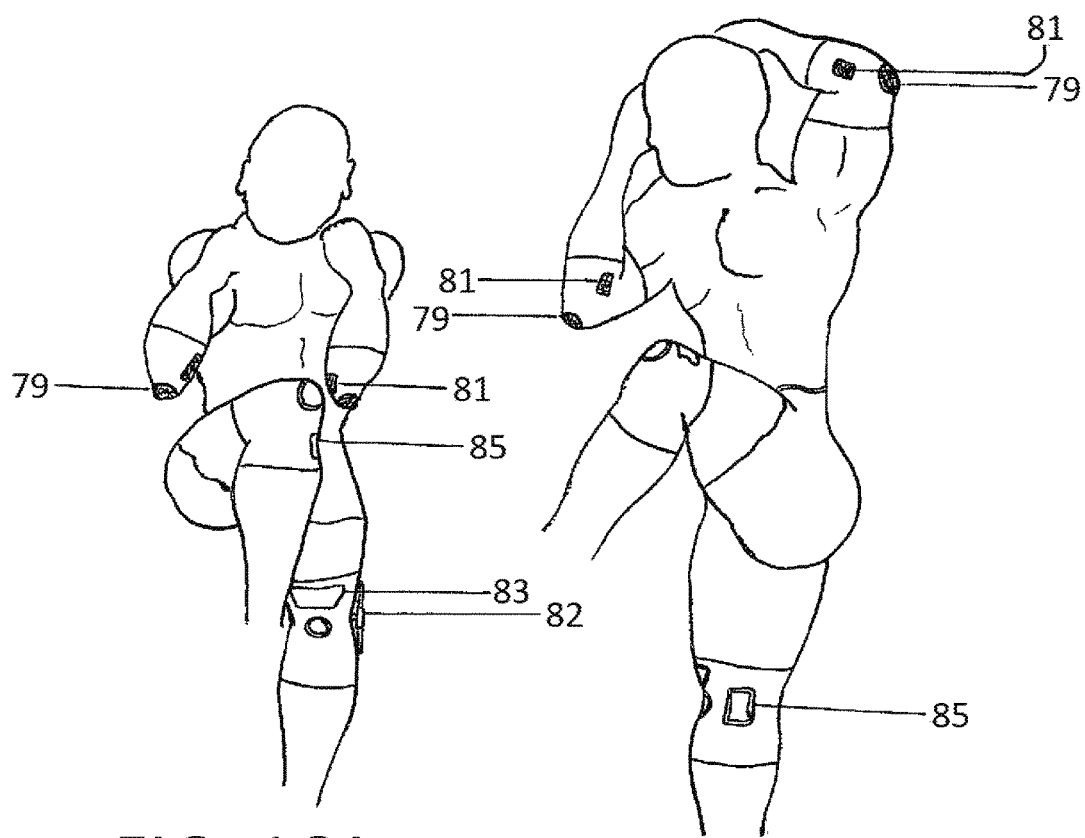

DIGITAL PROFESSIONAL TRAINING INSTRUCTOR (THE DPT INSTRUCTOR)

CROSS REFERENCE TO RELATED APPLICATIONS

This application claims the benefit of U.S. Provisional Patent Application No. 61/355,498, filed Jan. 8, 2010, incorporated by reference herein in its entirety.

TECHNOLOGICAL FIELD

Example embodiments of the present invention relate generally to consumer fitness electronics and, more particularly, to a system for providing accurate exercise instructional guidance.

BACKGROUND

Professional and celebrity fitness instructors are known to distribute instructional fitness media in which they teach audiences to perform various exercises and fitness routines. However, despite all efforts to emulate the posture and execution of the instructor, viewers of the media routinely fail to execute the associated movements properly.

Applicants have discovered a lack of personalized accessibility in traditional forms of fitness materials such as professional and celebrity instructional media. Through applied effort, ingenuity, and innovation, Applicants have solved many of these identified problems by developing a solution that is embodied by the present invention and described in detail below.

BRIEF SUMMARY

A novel system is provided in the form of the DPT instructor. The DPT instructor has been designed to capture the posture and execution technique of individuals. This is accomplished through recording posture of the limbs and form of execution technique in measurements of geometric angle degree movement trajectory calculations. The DPT instructor offers users that desire to emulate the precise and exact posture of execution technique of select instructors the ability to do so and with an accuracy and convenience that was previously unknown in the field of exercise fitness instruction devices.

In a first example embodiment, a system is provided for improved execution of fitness exercises. The system includes a DPT instructor apparatus for providing preprogrammed or programmable portable electronic fitness instructions. The system also includes a plurality of Timrek apparatuses configured to be fitted to a user physical joint, and configured to provide a measurement of a first geometric angled degree of posture as a first motion of the physical joint commences and upon reaching a pre-recorded geometric angled degree of posture, to provide a first signal, to the DPT apparatus, indicative of compliance and, subsequently, to provide a second measurement of a second geometric angled degree of posture as a second motion of the physical joint commences and upon reaching a second pre-recorded geometric angled degree of posture, to provide a second signal, to the DPT apparatus, indicative of compliance. The system also comprises knee and elbow cuff sleeves or braces, wherein the Timrek apparatuses are configured to attach to the knee and elbow cuff sleeves or braces. The system also comprises a panel transmitter system, being an upper knee and inner knee panel sequence device that is configured to attach to modified knee and elbow cuff sleeves or braces and register contact from corresponding elbow and inner forearm transmitters, the elbow and inner forearm transmitters configured to attach to the modified knee and elbow cuff sleeves or braces. The panel transmitter system comprises at least one display panel screen configured to display an illumination upon registering a prescribed contact between an upper knee and inner knee panel sequence device from the corresponding elbow and inner forearm transmitters.

In some embodiments, the DPT apparatus comprises a database of information comprising geometric angle measurements and touch sensory movement trajectory calculations associated with at least one instructor. The information in the database further comprises a systematic timing log for each of a plurality of fitness exercise workout routines.

In some embodiments, the database of information also comprises user-specific routine programs, monitoring, timing, and angling of the geometric angle degree measurements and the touch sensory movement trajectory settings associated therewith.

In some embodiments, the database of information also comprises exercise guidance instructions associated with the at least one instructor and a complete workout performance routine comprising timing.

In some embodiments, the database of information comprises one or more routines associated with a practitioner with a corresponding program associated with at least one instructor. The stored routine comprises at least one of recorded sets, timing, reps, or projected time for completion.

In some embodiments, the database of information comprises computerized voice instruction associated with a complete workout performance routine, configured to interactively count throughout each of the practitioners emulative workout programs repetitions as each are performed, registers errors, displays sets, and break time.

In some embodiments, the database of information further comprises posture of alignment and guidance instruction associated with at least one instructor.

In some embodiments, the DPT apparatus comprises a touch sensory movement trajectory calculation system to interactively guide and instruct the emulation of posture of execution techniques associated with the at least one instructor as the practitioner executes the selected preprogrammed or programmed fitness exercise routine and program performance.

In some embodiments, the database of information comprises a video log of prerecorded fitness exercise information, tips, and guidance instruction from at least one instructor teaching, advice, and application of use in correspondence to a portion of fitness exercises, fitness exercise machines, and fitness exercise devices.

In some embodiments, the database of information comprises instruction associated with at least one instructor.

In some embodiments, the DPT apparatus comprises one or more motion trackers to display the geometric angle degree measurement readings from a range of 0 to 180 degrees, and corresponding digitalized numerical degree readings. The motion trackers reflect and display the set prescribed geometric angle degrees determining and instructing the prescribed posture of execution and form technique. The motion trackers also reflect the practitioner's emulative and interactive posture of execution and form technique, which is displayed in measurements of geometric angle degrees in correspondence to a positioning of the Timrek apparatus.

In some embodiments, the DPT apparatus comprises a touch sensory movement trajectory calculation system to interactively guide and instruct emulation of posture of execution techniques and trajectory calculation instructions associated with at least one instructor. The touch sensory movement trajectory calculation system further provides programmed video guidance instruction related to posture of execution technique associated with at least one instructor, and tracking of the count, reps, and time.

In some embodiments, the DPT apparatus comprises a visual light sequence system that is used for a mute mode of the device. The visual light sequence system uses an interactive light illumination sequence that provides instruction to the practitioner throughout the entire execution phase of the fitness exercise routine.

In some embodiments, the visual light sequence system provides guidance throughout the execution of each of one or more fitness exercises, fitness exercise devices, machines, or variations.

In some embodiments, the visual light sequence system comprises green light signals, yellow light signals, red light signals, and bright white signals. The green light signals initiate the fitness exercise execution phase. The yellow light signals continue the fitness exercise execution phase. The red light signals stop or reverse the execution phase. The bright white light warns the practitioner that they are in error or are in an extreme and potentially injurious posture of performance.

In some embodiments, the DPT apparatus comprises functionality for interactively counting emulative fitness repetitions.

In some embodiments, the Timrek apparatus further comprises functionality enabling monitoring and guidance instruction using posture of execution technique, associated with at least one instructor, utilized and maintained when performing at least one of a given fitness exercise.

In some embodiments, the Timrek apparatus comprises converting formulations into geometric angle degree calculations, emulative formulation, tracking, guidance instruction, every motion and alternation as it alternates in correspondence to the limbs alternation, being via remote control signaling reflected and registered by an in motion tracker system of the DPT apparatus.

In some embodiments, the panel transmitter system is configured to utilize a web based circuitry system to communicate with the central electronic circuitry base of the Timrek apparatus and enable the panel transmitter system to register contact from elbow and inner forearm transmitters. The panel transmitter system can also forward one or more detections via remote control to the DPT apparatus to provide interactive, emulative executions, monitoring, and fitness exercise guidance instruction. The panel transmitter system, as the elbow and inner forearm (EIF) transmitters touch the panel transmitters, can register a contact as a fitness exercise repetition in accordance to programming. The panel transmitter system can then interact and respond to the contact amplifying by way of registering the corresponding contact between the two, wherein the panel transmitter and EIF transmitters being positioned in order to provide the DPT apparatus with a system of emulative or interactive fitness exercise guidance instruction predicated upon emulative execution technique as it is performed by at least one instruction workout routine performance that require or incorporate contact between the elbow or inner forearm and the upper knee or inner knee regions.

In some embodiments, the attaching device, when pressed due to improper posture to make contact with one another, the fitness repetition being nullified, the attaching device used as posture of executions monitoring devices when performing push-ups, the attaching device is programmed to operate in conformity with the Timrek apparatus and the panel transmitters. When space is compromised between themselves and the panel transmitter's upper knee surface, the repetition attempt registers as an error due to improper posture of execution technique.

In some embodiments, the system further comprises lower and upper torso cuff sleeves or braces along the outside of the arms and legs medial flexion joint regions. The Timrek apparatuses are configured to attach to the lower and upper torso cuff sleeves or braces.

BRIEF DESCRIPTION OF THE DRAWINGS

Figure 1:
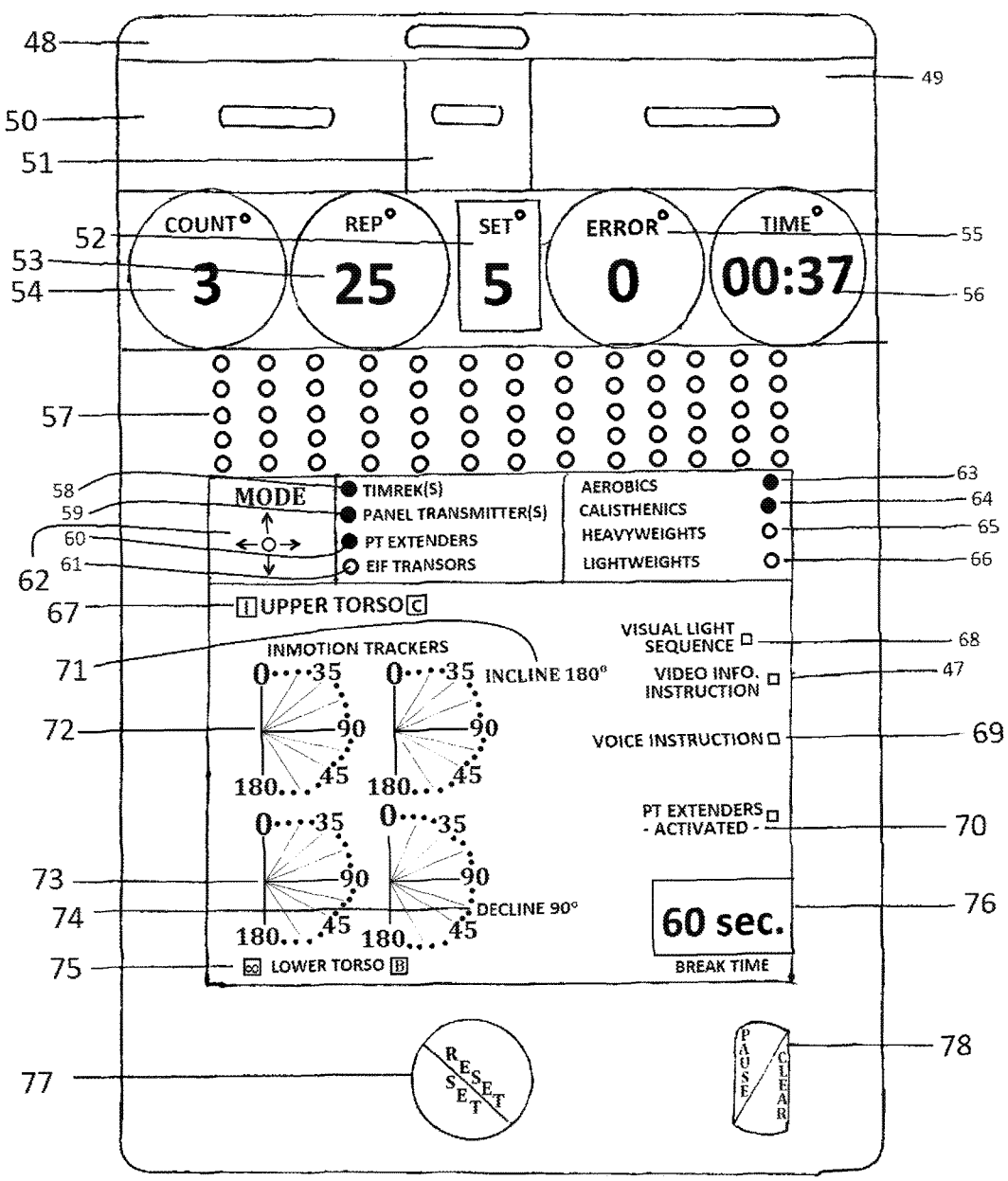

Having thus described certain example embodiments of the present disclosure in general terms, reference will now be made to the accompanying drawings, which are not necessarily drawn to scale, and wherein:

FIG. 1 shows an example depiction of a Digital Professional Training Instructor.

FIGS. 2A, 2B, and 2C illustrate three separate views of the upper torso cuff sleeves.

FIGS. 3A, 3B, and 3C illustrate two separate internal views of a Timrek.

FIGS. 4A, 4B, and 4C illustrate the method in which the Timrek maintains the ability to track, monitor, and instruct the user's workout routine as the Timrek moves in tandem with the position of the limbs during movement.

Figure 5:
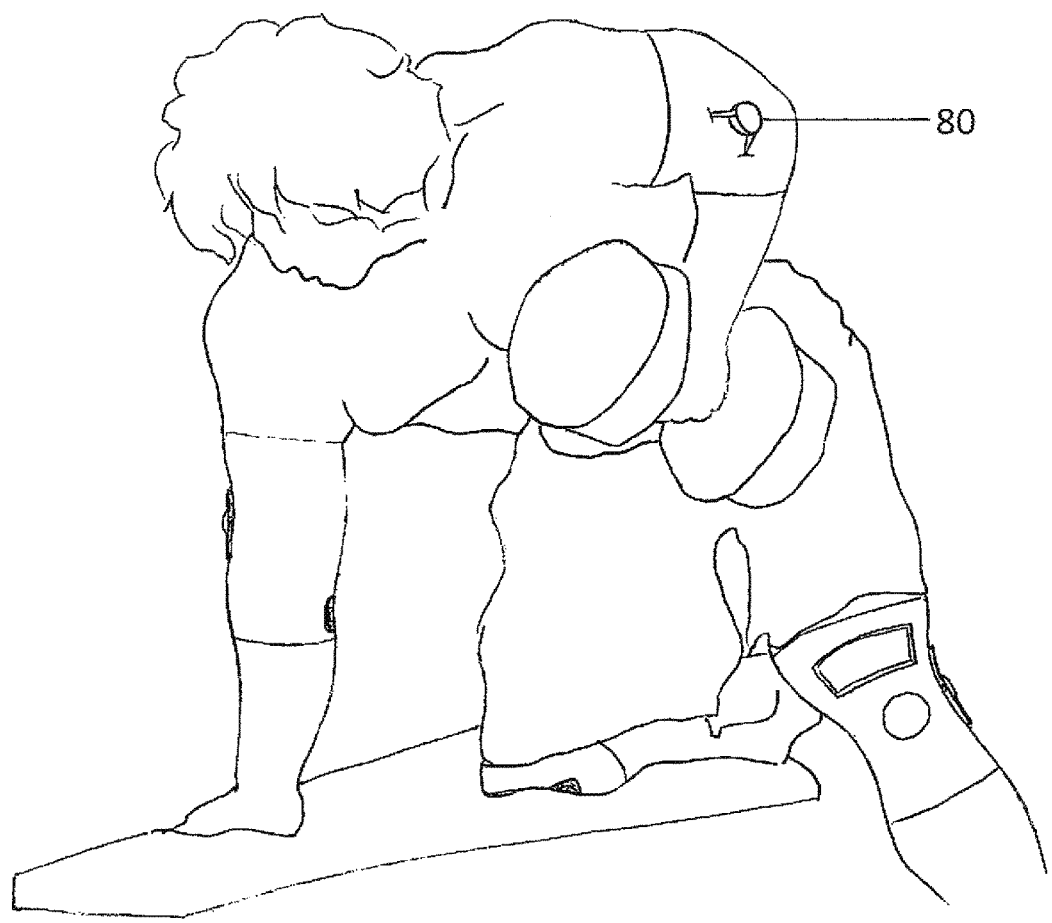

FIG. 5 illustrates an example usage of the Timrek.

Figure 6:
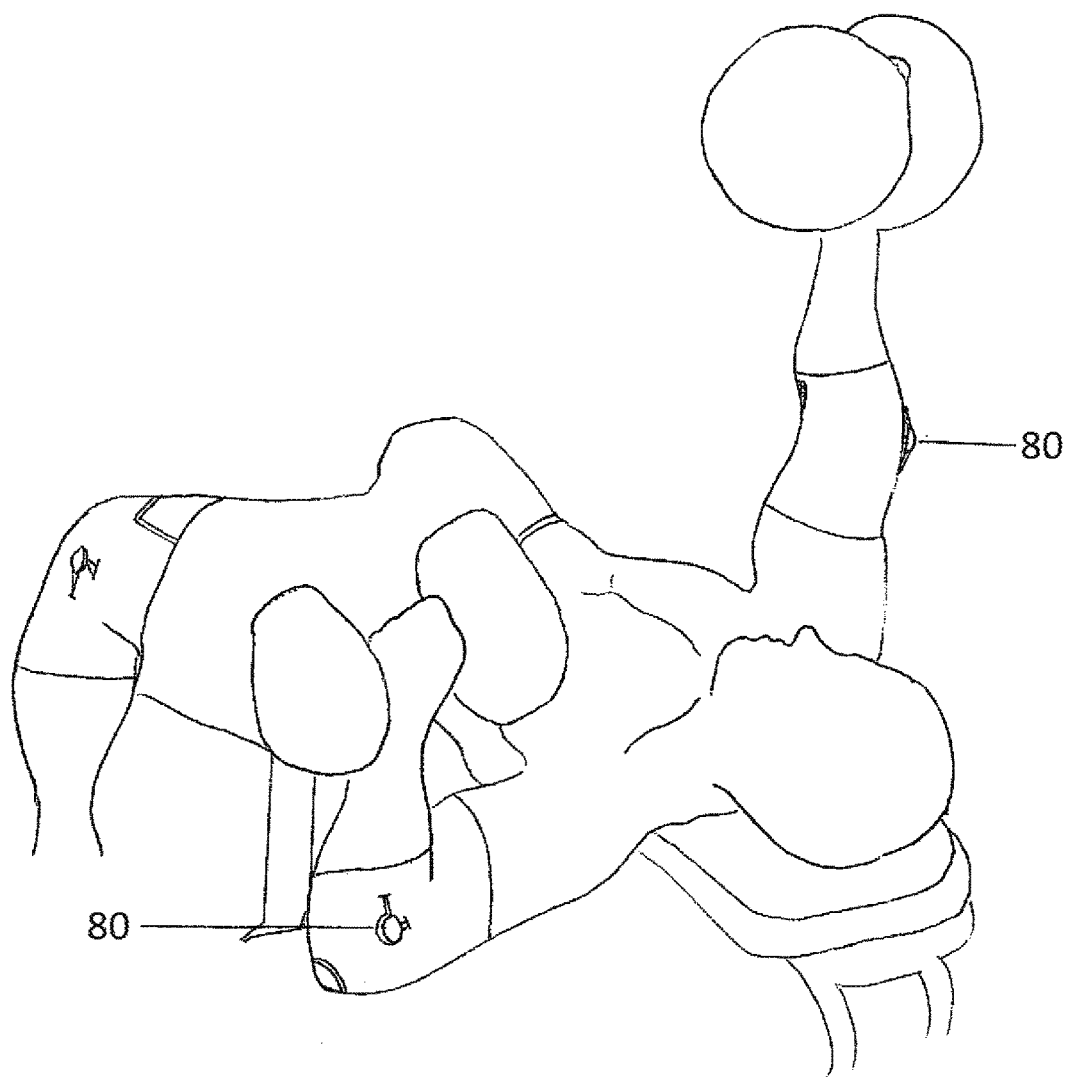

FIG. 6 illustrates an example usage of the Timrek by pinpointing accurate repetitions while the DPT instructor offers dual or individual Timrek guidance and monitoring instruction.

Figure 7:
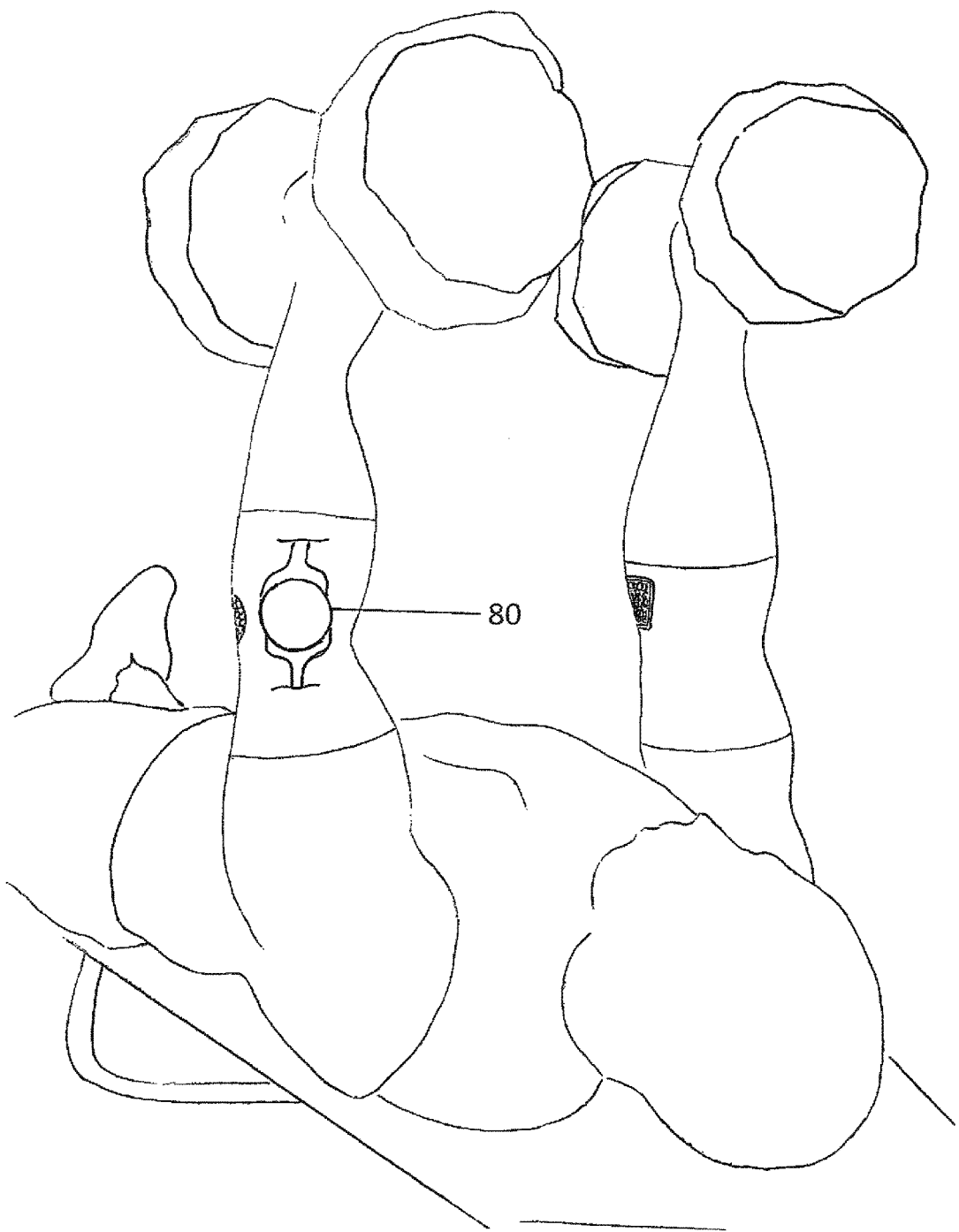

FIG. 7 illustrates an example embodiment in which a user is executing dual weight repetitions via Timrek and DPT instructor guidance monitoring.

Figure 8:
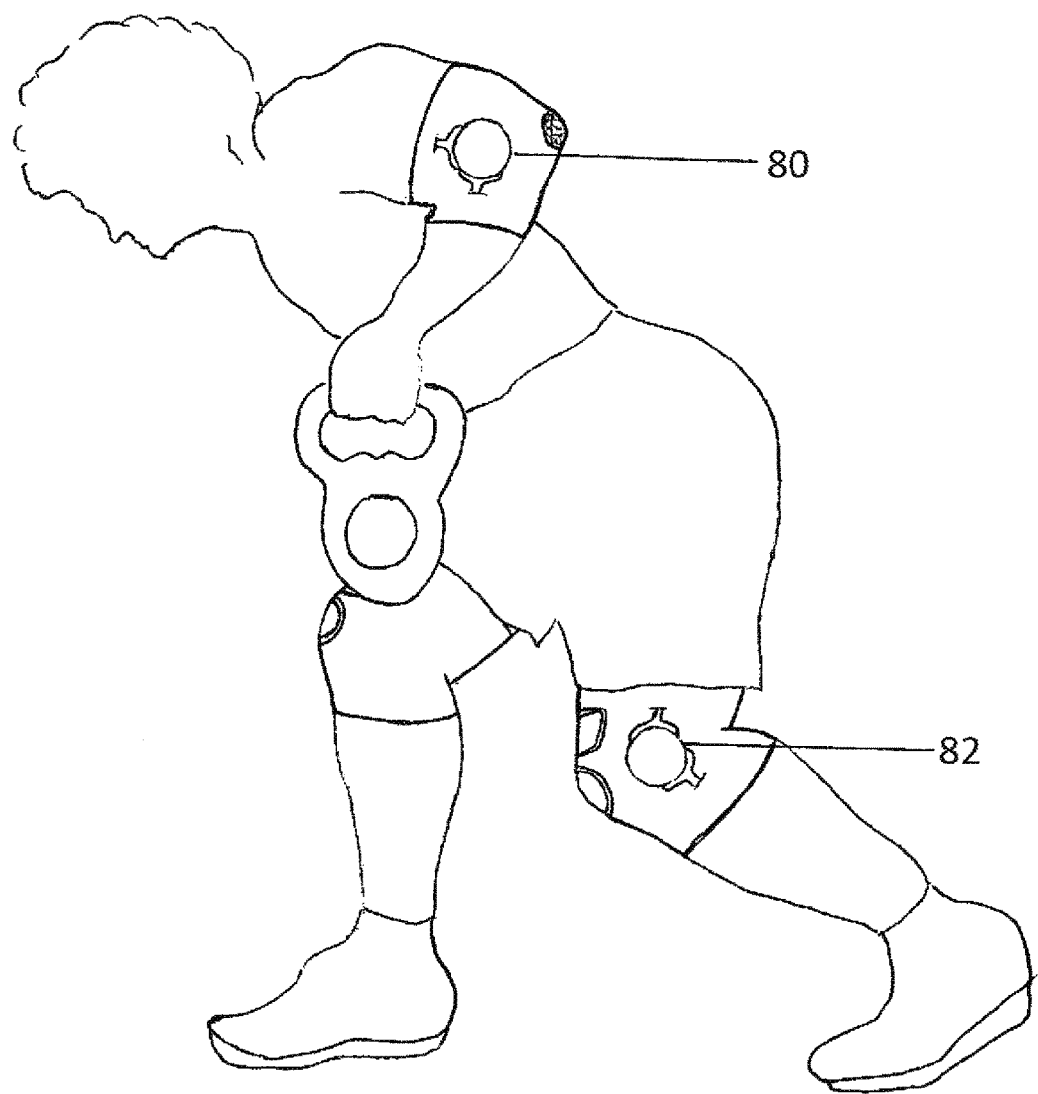

FIG. 8 illustrates an example usage of the Timrek.

Figure 9:
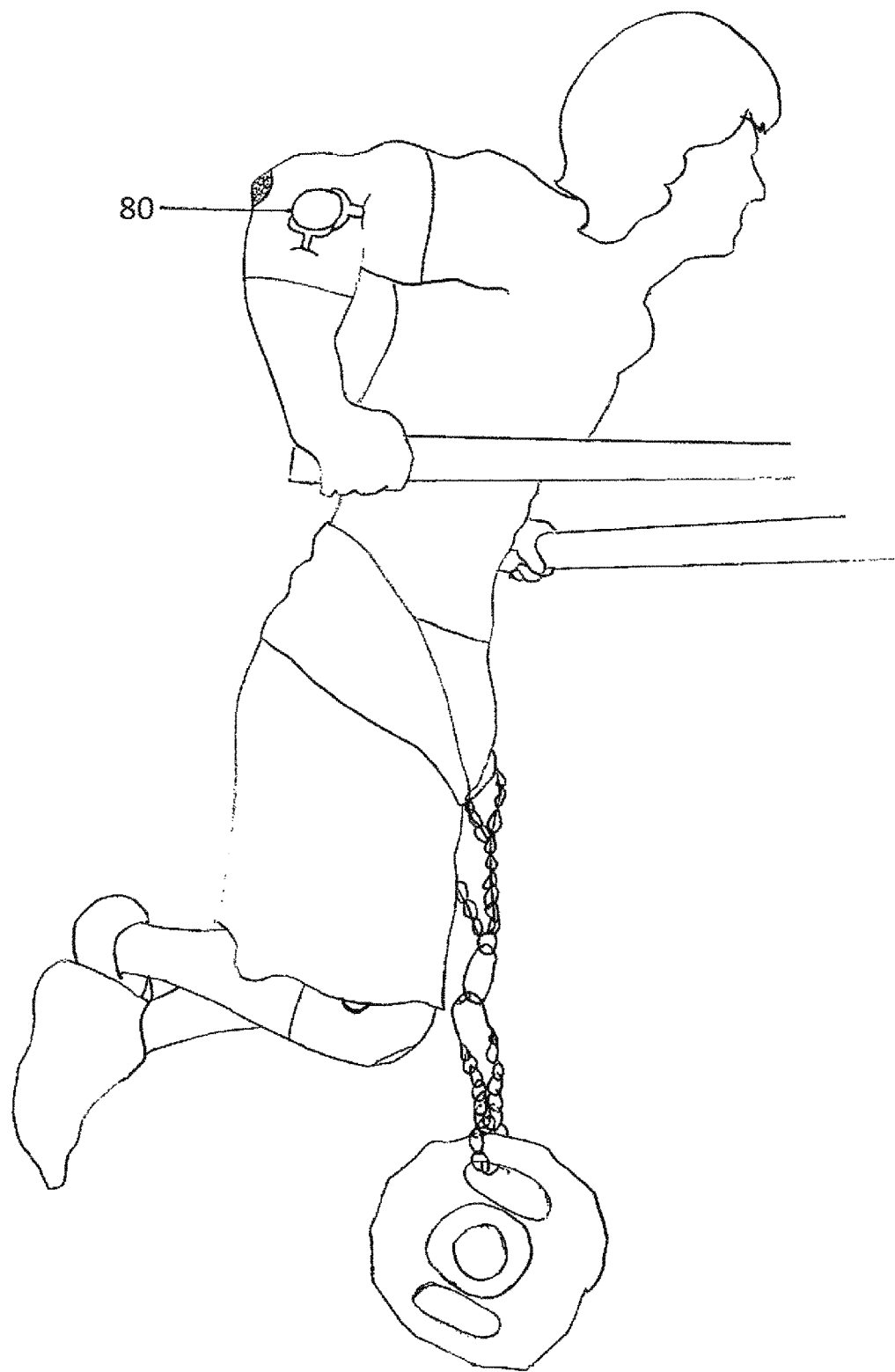

FIG. 9 an example embodiment of the Timrek being used in conjunction with other exercise equipment.

Figure 10:
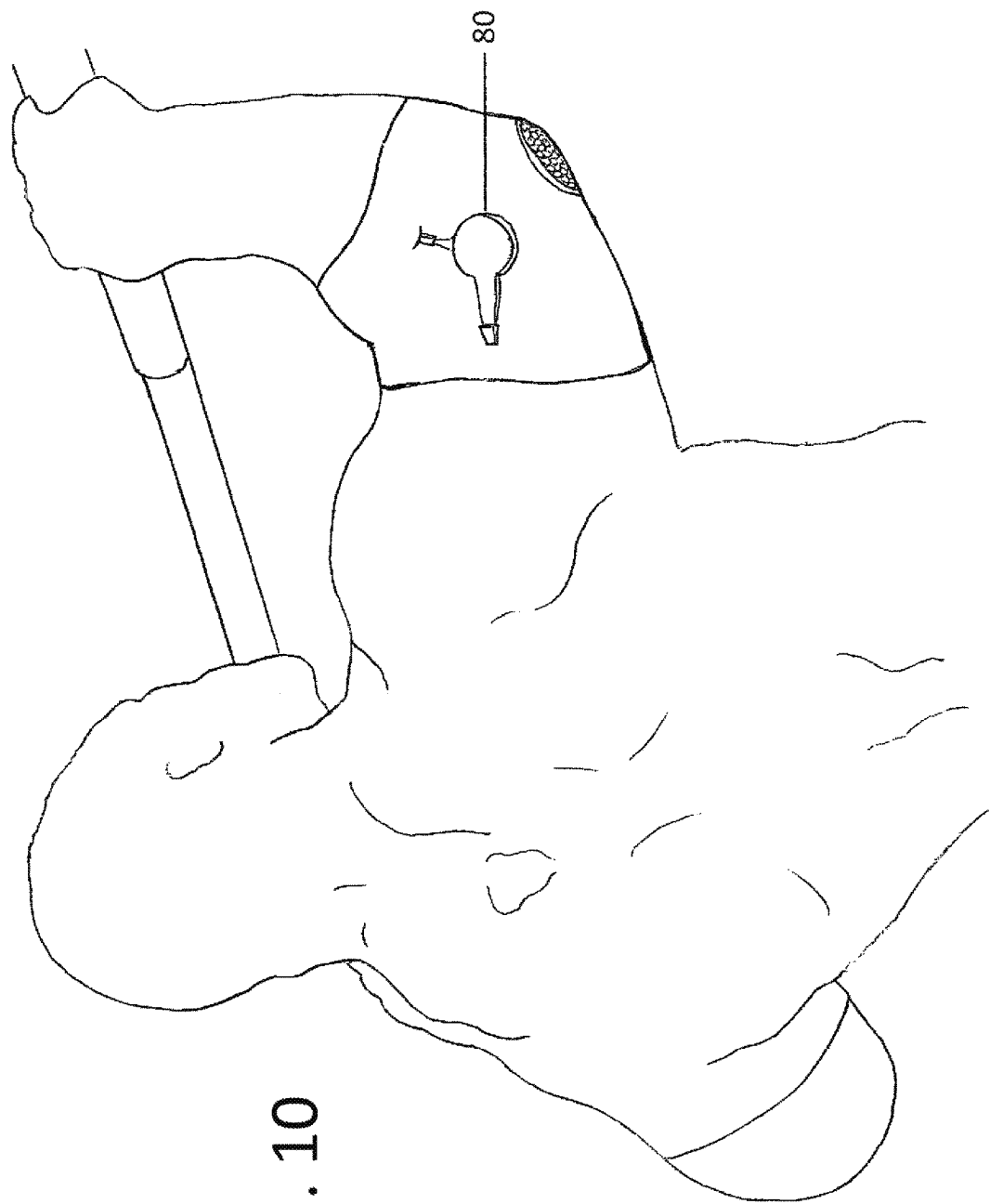

FIG. 10 illustrates an example embodiment wherein the user is performing pull-ups in accordance to a preprogrammed guidance instruction.

Figure 11:
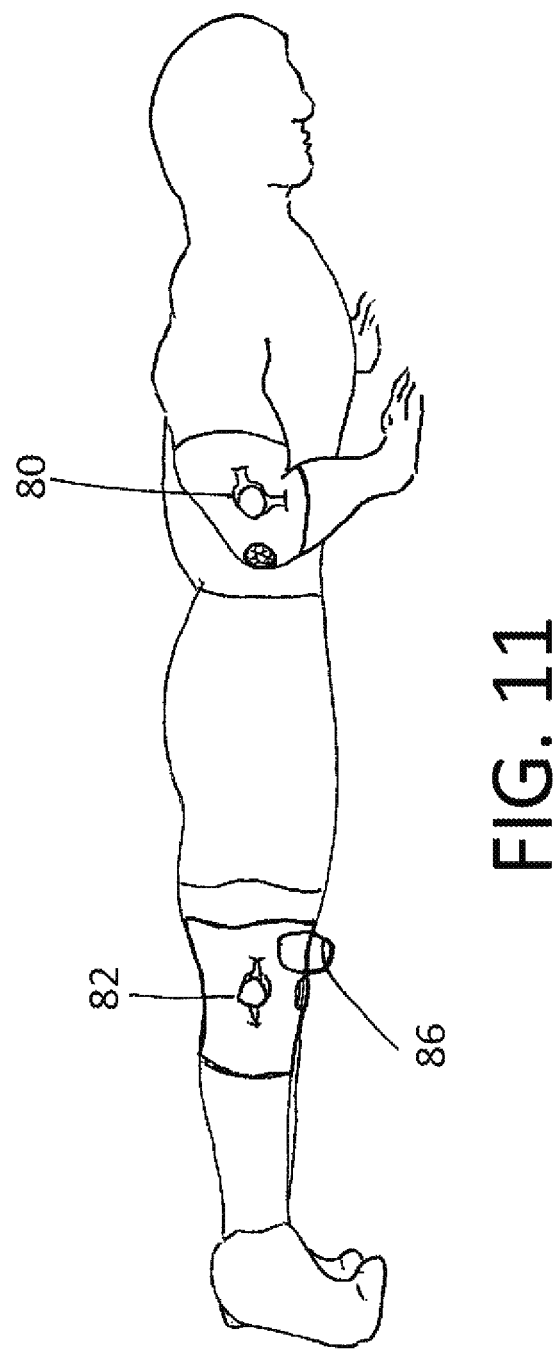

FIG. 11 illustrates an example embodiment wherein the user is performing push-ups while utilizing elbow and inner forearm transmitters.

FIGS. 12A, 12B, and 12C illustrate three separate views of the lower torso cuff sleeves.

FIGS. 13A and 13B illustrate the knee cuff Timreks and their ability to track and monitor posture and execution technique.

Figure 14:
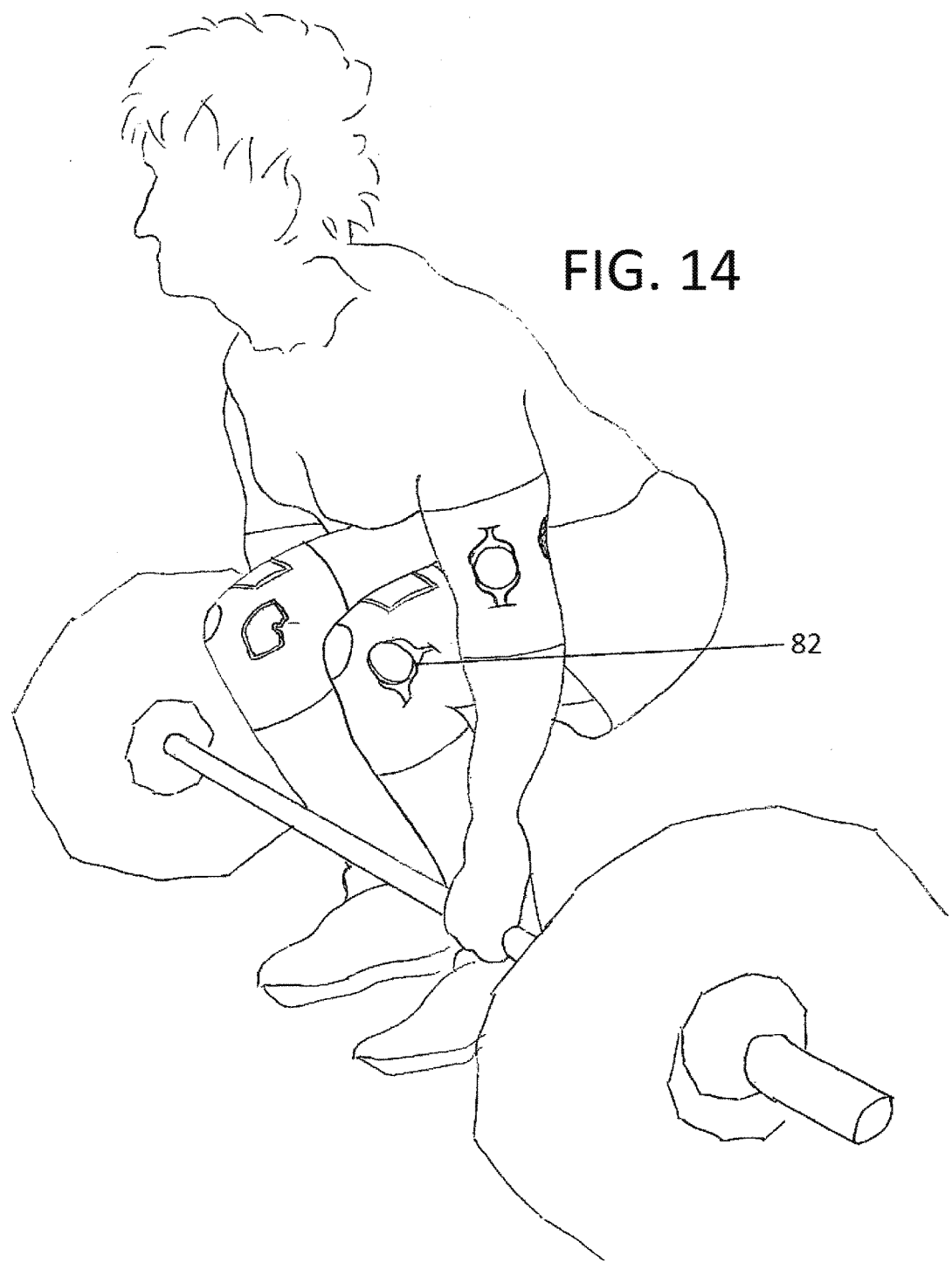

FIG. 14 illustrates an example embodiment wherein the user is performing weighted squats while utilizing the Timrek's tracking abilities.

FIGS. 15A and 15B illustrate an example embodiment wherein the user is performing cable pulls while the Timreks are corresponding to position changes.

FIGS. 16A and 16B illustrate an example embodiment wherein the user is performing aerobic exercises, while contact of the inner forearm transmitter with the inner knee panel transmitter registers on the DPT instructor.

Figure 17:
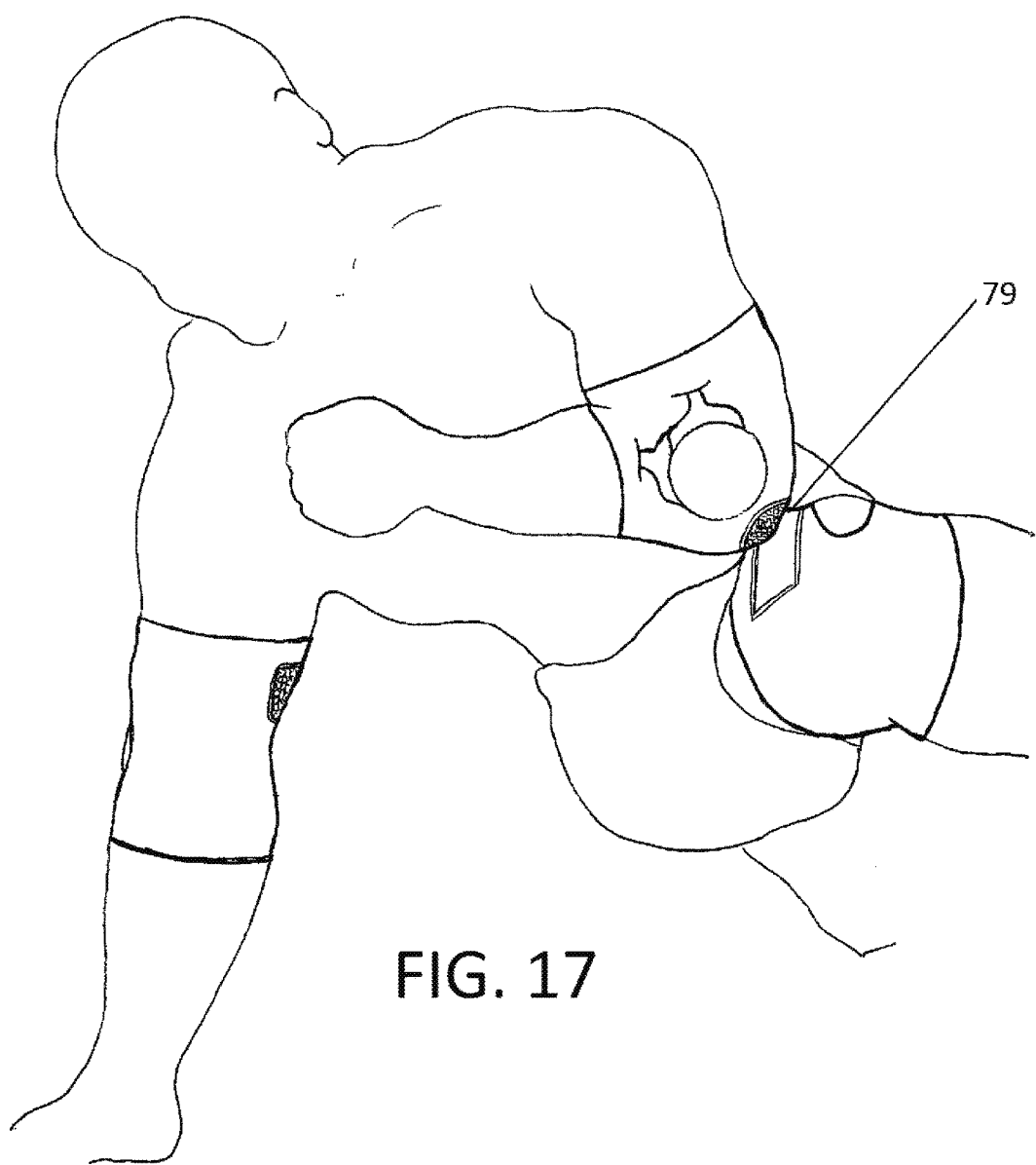

FIG. 17 illustrates an example embodiment wherein the user is performing aerobic exercises and touching the elbow transmitter to the panel transmitter.

Figure 18:
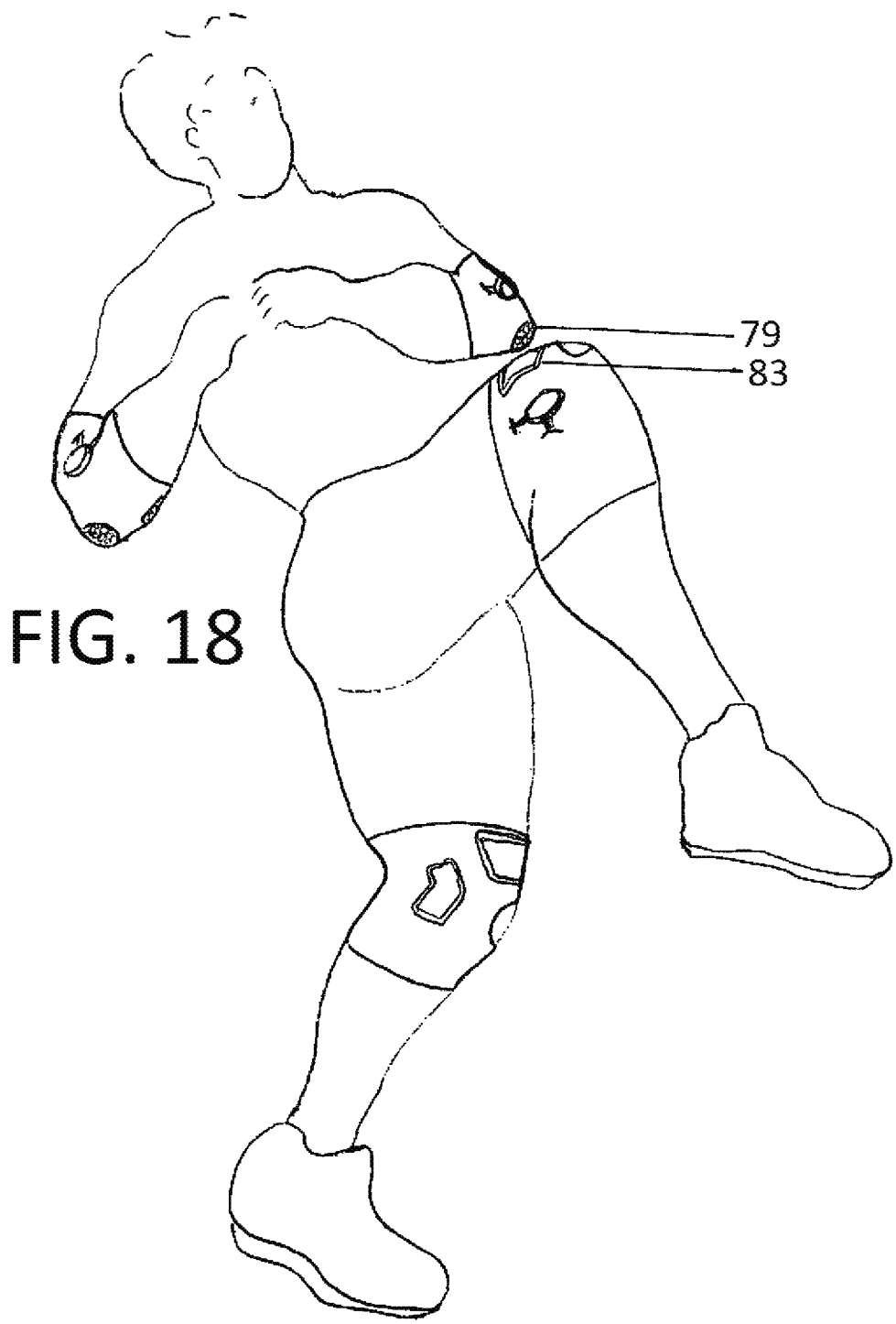

FIG. 18 illustrates an example embodiment wherein the user is performing aerobic exercises and touching the elbow to the upper knee panel transmitter.

Figure 19B:
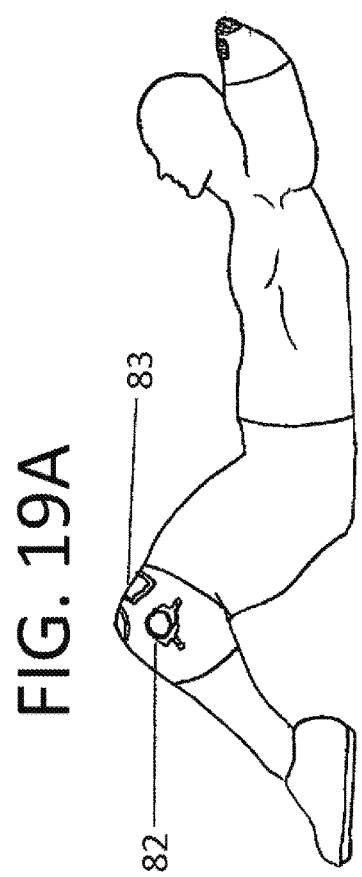
Figure 19A:
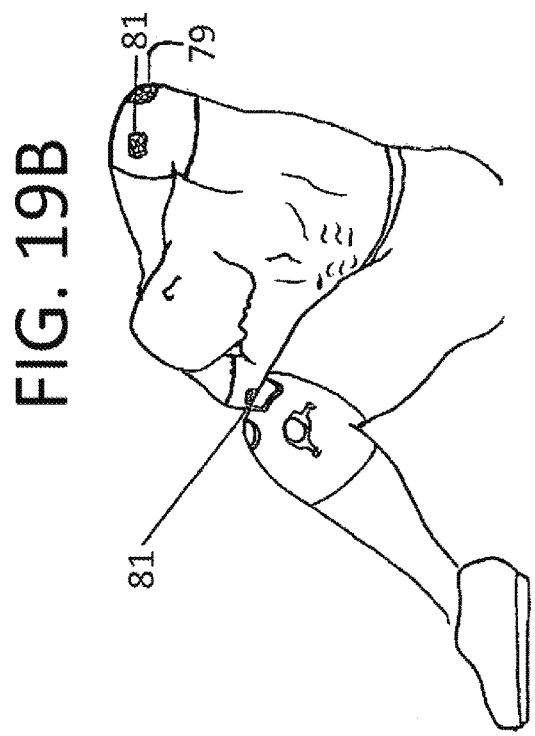

FIGS. 19A and 19B illustrates an example embodiment wherein the user is performing reverse sit-up exercises and making contact with the inner forearm transmitter and the inner knee panel transmitter.

Figure 20:
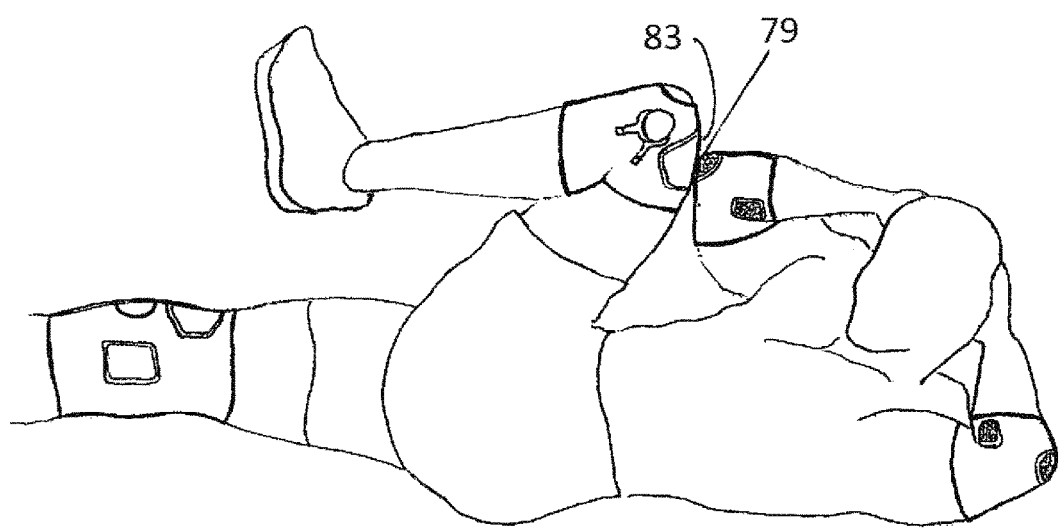

FIG. 20 illustrates an example embodiment wherein the user is performing reverse crunches utilizing the elbow transmitters, inner forearm transmitters, and panel transmitters.

DETAILED DESCRIPTION

Professional/Celebrity fitness instructors go to great lengths in their instructional media to teach and instruct their audiences. Yet, despite all efforts to emulate the instructor's execution and posture techniques, users of the instructional media fail from the inception or during the execution of the repetitions prescribed. To emulate a professional fitness instructor by viewing instructional media, such as a DVD, in no way compares to the hands-on guidance and instructor's personalized guidance instruction.

The DPT Instructor is intended to solve the problems of lack of accessibility to professional trainers and fitness instructors personalized exercise instruction guidance in which customers attempt to emulate via instructional media, as well as provide exercise monitoring, guidance, instruction, and conveniences that are able to be applied to virtually every exercise device, callisthenic, aerobic or type of workout selection variation.

The DPT Instructor brings a level of convenience, organization, instructional guidance, and accuracy that is rivaled by no other fitness device. This device uses the measurements of geometric angle degrees and movement trajectory calculations to guide and instruct the user's change of posture in the execution of exercises and maintains a log of the exercise program, along with offering visual and voice automated instruction guidance. The DPT Instructor not only brings the hands-on guidance instruction and a computerized accessibility of the exercise fitness practitioner(s) personal use, but it brings the instructor's personalized posture of execution technique to the user for unparalleled instructional guidance. The DPT Instructor accomplishes these feats with an accuracy that the celebrity/professional exercise fitness instructors could never equate nor rival themselves.

The DPT Instructor provides video screen instruction guidance to the user and this information comes from the endorsing or specified instructor. The instructor will offer tips, assistance, and instructional guidance execution information to the user. The DPT Instructor will, through digital tracking, display the prescribed exercise fitness posture of execution measurements and calculations of the practitioner's posture of execution technique as the exercise repetitions are being executed in geometric angle degree and movement trajectory calculations. The DPT Instructor will use the precise formula of measurements to guide and instruct the exerciser in the performance of programmed and preprogrammed exercise repetitions that are predetermined based upon professional/celebrity guidance instruction.

The DPT Instructor cannot be simply described as an exercise fitness device because it is so much more. The DPT Instructor is a personalized computer accurate professional/celebrity instructor's "fitness instructional counterpart" that is programmed to monitor, guide, instruct, and perfect a user's workout or fitness exercise routine in a way that no other device can. The DPT Instructor does in fact offer "Digital Professional Training Instruction".

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

FIG. 1 discloses an example Digital Professional Trainer Instructor apparatus. The Digital Professional Training Instructor (DPT instructor, henceforth) operates as a computerized version of a personal or celebrity fitness instructor. In the process of solving problems related to the lack of physical and personalized accessibility that fitness instructor media presents, the inventors of the DPT instructor have created a unique monitoring ability that extends to numerous fields including fitness, exercise, electronic fitness devices, exercise machines, and therapy.

The DPT instructor comprises elbow sleeves (FIGS. 2A, 2B, and 2C) and knee sleeves (FIGS. 12A, 12B, and 12C). In the laboratory programming and development phase of the DPT instructor, the process begins by recording a fitness instructor's physical posture and movement execution technique. This involves fitting the fitness instructor with the elbow and knee sleeves. Data will then be collected from the fitness instructor to program the device, in order to instruct the user and offer personal advice regarding execution techniques and expected results.

The Timrek 80 is a swiveling dihedral angle-like fitness exercise instruction and monitoring assistance apparatus comprising a central electronic circuitry base that enables the device to rotate from angles of 0 to 180 degrees. The Timrek, via remote control signaling, may forward, track, and match corresponding trajectory rotation calculations of preprogrammed, programmed, and executed fitness postures that are received by bending of the elbow or knee region in response to DPT instructor guidance. The Timrek 80 may attach to the elbow sleeves and knee sleeves. FIGS. 13-15 depict example embodiments of the Timrek attached to a knee sleeve.

The Timreks 80 may be comprised of a metallic and plastic compound. The Timreks 80, when attached to the sleeves, may move in precise alternation and motion as the respective limbs of the user during a motion or exercise. As limbs bend and flex, the changing postures are reflected digitally in the DPT instructor. Therefore, after a user selects a particular exercise listed in the DPT instructor to perform, the Timreks 80 will provide computer accurate fitness instruction on each repetition executed, so long as the repetitions comprise bending of the elbow or knee regions. Once the exercise selection has been made, the programmed measurements will place the limitations on the Timreks' 80 signaling system via remote control and will be dictated by the DPT instructor.

The fitness instructor will be providing this data by way of the Timrek's tracking ability to reflect posture changes via remote control signaling, in being situated alongside the elbow joint region and the knee joint region. FIGS. 4A, 4B, and 4C illustrate how the Timrek 80 maintains and simultaneously displays the changes in measurements of geometric angle degrees for tracking and instructional guidance purposes. Each measurement will be recorded based upon the instructor's performance of fitness exercises or in relation to the usage of fitness devices or workout machines.

Example embodiments can be seen in FIGS. 5-10, in which a Timrek 80 is being utilized while a user is performing various exercises.

FIG. 11 illustrates another example, wherein a fitness instructor, John Doe, will perform push-ups. First, John Doe will provide an audio and/or visual briefing of the selected exercise, tips for maximum results, and expected results. John Doe will then execute one repetition of the selected exercise. The laboratory personnel will record the posture of execution of John Doe, for example, as the following: Arms and Timrek's 80 on full extension incline measurement at a 175 degree angle, and on decline, a 90 degree angle. Therefore, when an individual using the DPT instructor is fitted with the elbow and knee sleeves and elects to perform the push-up exercise, the device will operate in the manner as described below.

When the individual presses the start button 77 and their arms extend to a 175 degree angle on incline, the Timrek 80 will send the signal reading to the DPT instructor and the device will produce an audible notification and instruction to proceed with the push-up motion. As the individual declines to a 90 degree angle, the device will again produce an audible notification and instruction to proceed with the next step of the push-up motion, such as, in this example embodiment, returning to a 175 degree angle. The device will then audibly indicate that a complete repetition has taken place by incrementing a counter 53 and stating the repetition count. At this point in the example embodiment, the device may audibly state, through the DPT instructor speaker system, "one" to indicate that one push-up has been completed.

A prescribed number of repetitions to perform may pertain to the exercise routine. Upon completion of the prescribed number of repetitions, the device may audibly indicate to the user to cease the movement. In this example embodiment, the device may audibly state, through the DPT instructor speaker system, "stop". Subsequently, a rest period will begin in which the user does not perform the exercise. Upon conclusion of the rest period, the device will produce an audible indication that it is time for the user to begin exercising again. In this example embodiment, the device may audibly state, through the DPT instructor speaker system, "next set".

The DPT Instructor may allow for display of various indicators for the user to select or view. In FIG. 1, the Mode button 62 may be used for cycling through and toggling different settings such as, for example, Timrek(s) 58, Panel Transmitters 59, PT Extenders 60, EIF Transmitters 61, Aerobics 63, Calisthenics 64, Heavyweights 65, and Lightweights 66. Other indicators may be present as well, such as, for example, indicators for Upper Torso 67, Visual Light Sequence 68, Video Information Instruction 47, Voice Instruction 69, PT Extenders Activated 70, Lower Torso 75, Break Time 76, Incline 71, and Decline 74. Angle settings 72 and 73 may also be provided for display. A Pause/Clear button 78 may also be present on the DPT instructor.

The pushups come with panel transmitter extenders. The panel transmitter extenders are attached apparatuses that function as touch sensor cancellation devices. The panel transmitter extenders, when connected to the panel transmitters, promote proper posture for various exercises by maintaining a user's prescribed form of execution. This is done by a touch sensory feature in the DPT instructor's push-up programming system that cancels out reps when the panel transmitter extenders are pressed to the panel transmitters due to improper posture or execution technique.

Pointing to FIGS. 16-20, the other feature that provides monitoring instruction guidance comes from the combination of the panel transmitters 83 and 85 and the elbow transmitters 79 and inner forearm transmitters 81. The panel transmitters 83 and 85 are upper knee and comprise an electrical sensory system that flows through the Timreks and enables the apparatus to register properly calculated exercise repetition by using preprogrammed and programmed formulas of movement trajectory touch sensory contact. The panel transmitters 83 and 85 are fiber-based compounds that comprise an electrical web-based sensory system that enables electrical currents to travel through to the Timreks, wherein the Timrek utilizes the Timrek's own central electrical sensory system to transfer, via remote control, every contact that is registered from the elbow and inner forearm transmitters with the panel transmitters to the DPT instructor.

For example, if a user selects aerobics 63 and the DPT instructor instructs the user to touch the inner forearm to the inner knee, then the DPT instructor's aerobic exercise program will require alternate touch "high knee" raises. This exercise may be coded as CC A-3 (Color Code Aerobics 3). Once CC A-3 has been programmed into the DPT instructor, a user may start the program. The DPT instructor will then present the time for completion 56 and prescribed repetitions 53. Upon completing a repetition, such as, for example, touching the inner forearm to the inner knee panel transmitter, an audible alert, such as a beep, may sound from the DPT instructor speaker system 57 to indicate contact. A repetition counter 53 may also be implemented in order to keep audible count of repetitions.

If the device is in mute mode, the specialized instructional guidance featured called the Visual Light Sequence is activated and the repetition process unfolds in the manner below.

For example, if a user selects "Squats Heavyweight Training Program, 250 lbs." under the guidance of DPT instructor John Doe, the selection may be coded under the formula of HWSS (heavy weights squats selection). As the routine commences, the green light of the visual light sequence system will turn on as the Timreks on the knee sleeves are extended by lifting the weight off of a bar brace. As the user commences the squat exercise and their legs bend on the decline, the yellow light will turn on, and as the prescribed descent level is reached, the red light will turn on, indicating to the user to stop descent. As the incline motion is commenced, the light will again turn yellow. As the legs are extended to the prescribed level on incline, the light will turn green, indicating to the user to commence descent once again. If, at any time, the user descends below the prescribed level, the white light 48 will activate and flash with warning. This system has been installed to guard against injury of the user. Upon completion of all prescribed repetitions, the green light 50, yellow light 51, and red light 49 will flash haphazardly indicating the completion of the set. The DPT instructor may display the executed sets 52, count 54, repetitions 53, errors 55, and time 56. Computerized voice instruction may audibly emit from the DPT instructor speaker system 57. All features shown on the automated voice instruction system are going to be displayed with the visual light sequence instruction system. The visual light sequence is a comprehensive instruction and guidance system that provides accurate fitness exercise instruction guidance and monitoring.

The DPT Instructor is the first and only exercise fitness device that is designed and equipped to capture the posture of execution technique and style of celebrity/professional exercise fitness instructors and instruct even the most inexperienced exercise fitness practitioners with the guidance that will enable them to perform pinpoint accurate movements during each and every repetition that is executed. The DPT Instructor is the only exercise fitness instruction device that bridges the gap between professional/celebrity fitness instructors and their audiences access to ensure exercise fitness instruction guidance and personalized accessibility.

In some embodiments, certain ones of the operations above may be modified or further amplified. Furthermore, in some embodiments, additional optional operations may be included. Modifications, amplifications, or additions to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What we claim as our invention is:

1. A system comprising:
a digital professional training (DPT) apparatus for providing preprogrammed or programmable portable electronic fitness exercise instruction;
a plurality of swiveling dihedral angle-like fitness exercise instruction, guidance, positioning, tracking, monitoring, calculating and form emulating technique apparatus (timrek apparatus) configured to be fitted to a user physical joint configured to provide a measurement of a first geometric angled degree of posture as a first motion of the physical joint commences and upon reaching a pre-recorded geometric angled degree of posture, to provide a first signal, to the DPT apparatus, indicative of compliance and, subsequently, to provide a second measurement of a second geometric angled degree of posture as a second motion of the physical joint commences and upon reaching a second pre-recorded geometric angled degree of posture, to provide a second signal, to the DPT apparatus, indicative of compliance;
knee and elbow cuff sleeves or braces,
wherein the timrek apparatus is configured to attach to the knee and elbow cuff sleeves or braces;
a panel transmitter system, the panel transmitter system being an upper knee and inner knee panel sequence device configured to attach to modified knee and elbow cuff sleeves or braces and register contact from corresponding elbow and inner forearm transmitters, the elbow and inner forearm transmitters configured to attach to the modified knee and elbow cuff sleeves or braces,
wherein the panel transmitter system comprises at least one display panel screen, the display panel screen configured to display an illumination upon registering a prescribed contact between an upper knee and inner knee panel sequence device from the corresponding elbow and inner forearm transmitters.

2. The system according to claim 1, wherein the DPT apparatus further comprises: a database of information, the information comprising geometric angle measurements and touch sensory movement trajectory calculations associated with at least one instructor;
the information further comprising a systematic timing log for each of a plurality of fitness exercise workout routines.

3. The system according to claim 2, wherein the database of information further comprises user-specific routine programs, monitoring, timing and angling of the geometric angle measurements and the touch sensory movement trajectory settings associated therewith.

4. The system according to claim 2, wherein the database of information further comprises exercise guidance instructions associated with the at least one instructor and a complete workout performance routine comprising timing.

5. The system according to claim 2, wherein the database of information further comprises one or more routine associated with a practitioner with a corresponding program associated with the at least one instructor, the one or more routine comprising at least one of recorded sets, timing, reps and projected time for completion.

6. The system according to claim 4, wherein the database of information further comprises a computerized voice instruction associated with the complete workout performance routine, configured to interactively count throughout each of the practitioners emulative workout programs repetitions as each are performed, registers errors, displays sets, and break time.

7. The system according to claim 2, wherein the database of information further comprises posture of alignment and guidance instruction associated with the at least one instructor.

8. The system according to claim 7, wherein the DPT apparatus further comprises a touch sensory movement trajectory calculation system configured to interactively guide and instruct the emulation of posture of execution techniques associated with the at least one instructor.

9. The system according to claim 1, wherein the database of information further comprises a video log of prerecorded instructional fitness exercise information, tips and guidance instruction from the at least one instructor teaching, advice and application of use in correspondence to a portion of fitness exercises, fitness exercise machines, and fitness exercise devices.

10. The system according to claim 1, wherein the DPT apparatus further comprises of one or more in motion trackers to display the geometric angle measurement readings from a range of 0 to 180 degrees and corresponding digitalized numerical degree readings.

11. The system according to claim 1, wherein the DPT apparatus further comprises a touch sensory movement trajectory calculation system to interactively guide and instruct emulation of posture of execution techniques, and trajectory calculation instructions associated with at least one instructor, the touch sensory movement trajectory calculation system, the touch sensory movement trajectory calculation system further providing programmed video guidance instruction related to posture of execution technique associated with the at least one instructor, and automated and interactive tracking of the count, reps, and time.

12. The system according to claim 1, wherein the DPT apparatus further comprises a visual light sequence system that is used for a mute mode of the device, the visual light sequence system to use an interactive light illumination sequence that provides instruction to the practitioner throughout the entire execution phase of the fitness exercise routine.

13. The system according to claim 12, wherein the visual light sequence system provides guidance throughout the execution of each of one or more fitness exercise, fitness exercise device, machine or variation.

14. The system according to claim 12, wherein the visual light sequence systems comprise green light signals, yellow light signals, red light signals, and bright white signals, the green light signals initiate the fitness exercise execution phase, the yellow light signals continue the fitness exercise execution phase, the red light signals stop or reverse the execution phase and the bright white light warns the practitioner that they are in error or are in an extreme and potentially injurious posture of performance.

15. The system according to claim 1, wherein the DPT apparatus further comprises functionality for interactively counting emulative fitness repetitions.

16. The system according to claim 1, wherein the timrek apparatus further comprises functionality enabling monitoring and guidance instruction using posture of execution technique, associated with at least one instructor, utilized and maintained when performing at least one of a given fitness exercise.

17. The system according to claim 1, wherein, the panel transmitter system is configured to utilize a web based circuitry system to communicate with the central electronic circuitry base of the timrek apparatus and enable the panel transmitter system to register contact from elbow and inner forearm transmitters (EIF Transmitters);

sending a signal indicative of one or more detections via remote control to the DPT apparatus to provide interactive, emulative executions, monitoring, and fitness exercise guidance instruction;

as the elbow and inner forearm transmitters (EIF transmitters) touch the panel transmitters, register a contact as a fitness exercise repetition;

wherein the one or more detections causing the panel transmitter system to interact and respond to the contact between the EIF transmitters and the panel transmitters.

18. The system according to claim 17, further comprising of:

a PT extender attachable to the Panel Transmitter, that cancels registration of an exercise when the PT extender touches the panel transmitter.

* * * * *